US012662376B2

(12) United States Patent　　　(10) Patent No.:　US 12,662,376 B2

Mattke et al.　　　(45) Date of Patent:　Jun. 23, 2026

(54) METHOD OF SEPARATING PHOSGENE AND HYDROGEN CHLORIDE

(71) Applicant: BASF SE, Ludwigshafen am Rhein (DE)

(72) Inventors: Torsten Mattke, Ludwigshafen am Rhein (DE); Kai Thiele, Antwerp (BE); Jens Ferbitz, Ludwigshafen am Rhein (DE); Peter Van Den Abeel, Antwerp (BE); Hans-Juergen Pallasch, Ludwigshafen am Rhein (DE)

(73) Assignee: BASF SE, Ludwigshafen am Rhein (DE)

( * ) Notice:　Subject to any disclaimer, the term of this patent is extended or adjusted under 35 U.S.C. 154(b) by 502 days.

(21) Appl. No.:　18/277,415

(22) PCT Filed:　Feb. 10, 2022

(86) PCT No.:　PCT/EP2022/053214

§ 371 (c)(1),
(2) Date:　Aug. 16, 2023

(87) PCT Pub. No.: WO2022/175152

PCT Pub. Date: Aug. 25, 2022

(65)　　　Prior Publication Data

US 2024/0300817 A1　　Sep. 12, 2024

(30)　　Foreign Application Priority Data

Feb. 17, 2021　(EP) ..................................... 21157533

(51) Int. Cl.
*C01B 7/07*　　　(2006.01)
*B01D 53/00*　　(2006.01)
(Continued)

(52) U.S. Cl.
CPC .......... *C01B 7/0712* (2013.01); *B01D 53/002* (2013.01); *C01B 7/0731* (2013.01); (Continued)

(58) Field of Classification Search
CPC ..... C01B 7/0712; C01B 7/0731; C01B 32/80; B01D 53/002; B01D 2256/26; B01D 2257/2064; C07C 263/20
See application file for complete search history.

(56)　　　　　References Cited

U.S. PATENT DOCUMENTS

| | | | |
|---|---|---|---|
| 7,504,533 B2 | 3/2009 | Bohm et al. | |
| 2006/0123842 A1 | 6/2006 | Sohn et al. | |
| | (Continued) | | |

FOREIGN PATENT DOCUMENTS

| | | |
|---|---|---|
| CN | 1729169 A | 2/2006 |
| CN | 107428542 A | 12/2017 |
| | (Continued) | |

OTHER PUBLICATIONS

International Search Report and Written Opinion received for PCT Patent Application No. PCT/EP2022/053214, mailed on Jun. 23, 2022, 10 pages.

(Continued)

*Primary Examiner* — Anthony J Zimmer
*Assistant Examiner* — Syed T Iqbal
(74) *Attorney, Agent, or Firm* — Faegre Drinker Biddle & Reath LLP

(57)　　　　　ABSTRACT

A process of separating phosgene and hydrogen chloride, comprises: conveying a mixed stream containing hydrogen chloride and phosgene into a distillation column; withdrawing from the distillation column a bottom stream containing phosgene; withdrawing a top stream containing hydrogen chloride; compressing at least a portion of the top stream and at least partially condensing the compressed top stream to (Continued)

form a liquid stream, decompressing at least a portion of the liquid stream to form a cooled liquid stream and a cooled gas stream; and recycling the cooled liquid stream to the top of the distillation column as a reflux; the process additionally comprising temporarily introducing an absorbing solvent into the distillation column, in particular during starting-up and/or shutting-down of the process. The process allows for safe operation even when hydrogen chloride production only gradually begins or decreases, without the necessity of storing hydrogen chloride.

11 Claims, 1 Drawing Sheet

(51) Int. Cl.
    *C01B 32/80*     (2017.01)
    *C07C 263/20*     (2006.01)
(52) U.S. Cl.
    CPC ............ *C01B 32/80* (2017.08); *C07C 263/20* (2013.01); *B01D 2256/26* (2013.01); *B01D 2257/2064* (2013.01)

(56) References Cited

U.S. PATENT DOCUMENTS

| | | |
|---|---|---|
| 2009/0209784 A1 | 8/2009 | Lorenz et al. |
| 2018/0044179 A1* | 2/2018 | Schelling .............. C01B 7/0712 |
| 2020/0148630 A1 | 5/2020 | Knauf et al. |

FOREIGN PATENT DOCUMENTS

| | | |
|---|---|---|
| EP | 3268349 A1 | 1/2018 |
| EP | 3653604 A1 | 5/2020 |
| WO | 2005/115974 A1 | 12/2005 |
| WO | 2016/142475 A1 | 9/2016 |

OTHER PUBLICATIONS

European Search Report for EP Patent Application No. 21157533.7, Issued on Jul. 30, 2021, 3 pages.
Six et al., "Chapter 4: Production," Isocyanates, Organic—Ullmann's Encyclopedia of Industrial Chemistry, 7th Edition, vol. 20, Jan. 15, 2003, pp. 70-76.

* cited by examiner

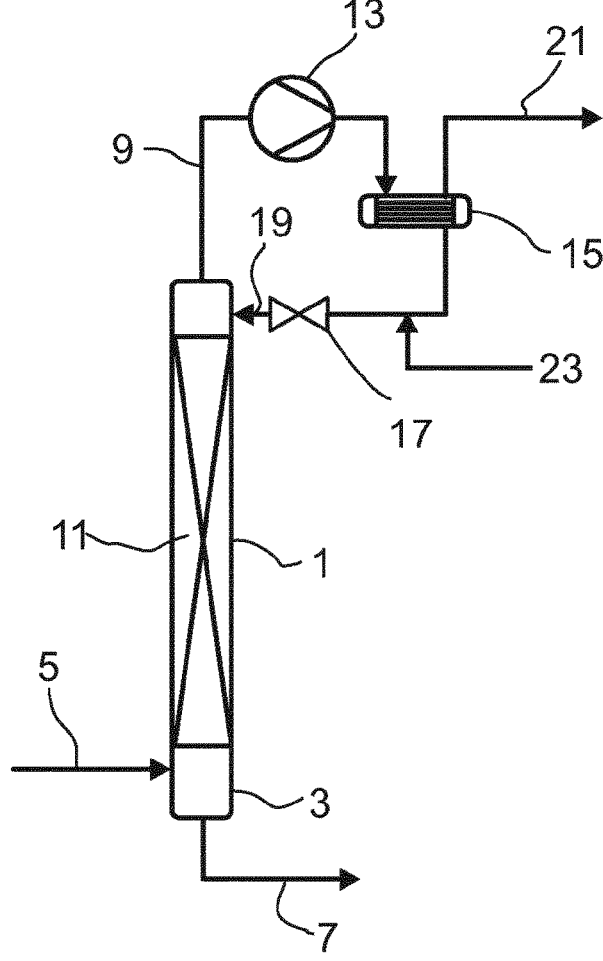

1

METHOD OF SEPARATING PHOSGENE AND HYDROGEN CHLORIDE

CROSS-REFERENCE TO RELATED APPLICATIONS

This application is a National stage application (under 35 U.S.C. § 371) of PCT/EP2022/053214, filed Feb. 10, 2022, which claims benefit of European Application No. 21157533.7, filed Feb. 17, 2021, both of which are incorporated herein by reference in their entirety.

The invention relates to a method of separating a mixed stream containing hydrogen chloride and phosgene.

Mixed streams containing hydrogen chloride and phosgene are generated, in particular, in the work-up of product streams from isocyanate production in a phosgenation reaction. Organic isocyanates such as methylene diphenyl diisocyanate (MDI) or toluene diisocyanate (TDI) are usually prepared from primary amines and a stoichiometric excess of phosgene. In addition to the desired isocyanate, hydrogen chloride is produced as a by-product.

Phosgenation may be carried out in a very wide variety of ways, for example as a gas phase phosgenation, cold-hot phosgenation, single-stage liquid phosgenation, hydrochloride phosgenation or gas/liquid phosgenation. A common feature to all reactions is that a stoichiometric excess of phosgene is used in order to avoid urea formation from the formed isocyanate and amine. Phosgenation methods are described, for example, in Ullmann's Encyclopedia of Industrial Chemistry, Chapter "Isocyanates, Organic", Chapters 4.1 and 4.2 (Six, C. and Richter, F., 2003). Inert media or solvents may be used depending on the type of method employed. The reaction mixture comprises essentially the isocyanate or precursors thereof, for example carbamyl chlorides, the hydrogen chloride formed, the excess phosgene and any inert media and/or solvents added.

There is a variety of uses for the hydrogen chloride by-product. For instance, the hydrogen chloride may be subjected to oxidative dehydrogenation, for example by the Deacon or Kelchlor processes, or to electrolysis, to obtain chlorine for the synthesis of fresh phosgene. The hydrogen chloride may further be used in oxychlorinations. Absorption in water to obtain aqueous hydrochloric acid is also possible.

Irrespective of the type of work-up, the hydrogen chloride is removed from the product mixture substantially simultaneously with the excess phosgene. Due to the significant phosgene excesses employed, recovery of the phosgene and return thereof into the process is necessary to ensure the very economic viability of the methods. Separation of hydrogen chloride and phosgene is therefore an essential component of isocyanate production methods based on phosgenation.

Various processes are known for the separation of hydrogen chloride and phosgene. Absorption or distillation methods are the most commonly used.

Absorption utilizes an absorbing solvent to scrub out phosgene from a gaseous mixed stream containing hydrogen chloride and phosgene, see e.g. U.S. Pat. No. 7,504,533.

The large boiling-point difference between hydrogen chloride and phosgene permits distillative separation but, due to the high vapor pressure of hydrogen chloride, necessitates separation at low overhead temperatures or a high pressure. Often, distillative separation is carried out at increased pressure in order to avoid too low head temperatures and the necessary provision of cryogenic cooling.

The distillative process described in application EP 3268349 or WO 2016/142475A relies on the compression of hydrogen chloride, in which a part of the compressed hydrogen chloride condenses and after decompression acts as reflux for the distillation. This allows very low temperatures in the column top and distillation at low pressure to be achieved. The condensation of the compressed hydrogen chloride, on the other hand, can take place at a higher temperature and places lower demands on the required degree of refrigeration.

Although the process has great advantages in steady operation, its start-up is tricky. Evidently, there is no hydrogen chloride available at the beginning as a reaction product of the phosgenation. Therefore, no reflux of liquid hydrogen chloride can be generated. When phosgenation is started, hydrogen chloride is gradually produced and the system can be filled. However, without reflux, phosgene ascends into the column head and may enter the compressor. This would result in existing safety concepts having to be revised, and would require additional, technical and cost-intensive safety measures. For downstream processing, the hydrogen chloride obtained has to meet specific purity requirements, especially in the case of use for oxychlorination or for the Deacon process. Hence, the hydrogen chloride released during the start-up period has to be discarded if there is insufficient reflux of liquid hydrogen chloride. Furthermore, compressors often require a minimum volume of gaseous hydrogen chloride to be started up.

In the simplest case, a supply of high pressure hydrogen chloride from a network or other already running plants is available at the plant site. Then the return system can be started up with extraneous hydrogen chloride. Frequently, however, stand-alone plants are installed or a mutual connection of the plant is undesirable. In principle, it is then possible to install a hydrogen chloride buffer which is filled during a normal driving period and which could then enable the return line to be started up with hydrogen chloride. However, both gaseous buffers, either pressureless or pressured, and cooled liquid buffers are very expensive to purchase and create safety scenarios that must be secured by appropriate and cost-intensive measures.

Accordingly, it was the object of the present invention to devise a process for starting a hydrogen chloride/phosgene separation with vapor compression and condensation, which involves low costs and creates no additional safety risks.

The invention provides a process of separating phosgene and hydrogen chloride, comprising:

conveying a mixed stream containing hydrogen chloride and phosgene into a distillation column;

withdrawing from the distillation column a bottom stream containing phosgene;

withdrawing a top stream containing hydrogen chloride;

compressing at least a portion of the top stream and at least partially condensing the compressed top stream to form a liquid stream, decompressing at least a portion of the liquid stream to form a cooled liquid stream and a cooled gas stream; and recycling the cooled liquid stream to the top of the distillation column as a reflux;

the process additionally comprising temporarily introducing an absorbing solvent into the distillation column, wherein the absorbing solvent is introduced at the top of the distillation column and/or into the reflux liquid.

The process may include recycling also the cooled gas stream to the distillation column at any point of the distillation column. Conveniently however, a two-phase liquid/gaseous stream obtained upon decompression of the liquid stream is introduced to the top of the distillation column.

The absorbing solvent which is introduced into the distillation column scrubs down phosgene that ascends in the distillation column. Generally, the amount of the absorbing solvent is controlled to limit the concentration of phosgene in the top stream to a predetermined concentration. Preferably, the amount of the absorbing solvent is controlled to limit the concentration of phosgene in the top stream to less than 5% by volume, preferably less than 1% by volume, particularly preferably less than 0.1% by volume.

Generally, the absorbing solvent can be introduced into the distillation column at any time during the process for scrubbing down phosgene ascending in the distillation column. Beside the temporarily addition of absorbing solvent, it may be also conceivable to introduce the absorbing agent for a longer time period during standard operation or for the complete time period under standard operation of the distillation column respectively the process, leading to an effective, easy to use and cost efficient process for separating phosgene and hydrogen chloride. Standard Operation in context of the present invention means any operating point or operating period after starting-up and before shutting down the distillation column respectively the process.

Preferably, the absorbing solvent is introduced into the distillation column during starting-up and/or shutting-down of the process.

Hence, in a preferred embodiment the invention relates to a process for starting-up a phosgene and hydrogen chloride separation process, comprising:

conveying a mixed stream containing hydrogen chloride and phosgene into a distillation column;
  introducing a stream of an absorbing solvent into the distillation column;
  withdrawing from the distillation column a bottom stream containing phosgene and absorbing solvent;
  withdrawing a top stream containing hydrogen chloride;
  compressing at least a portion of the top stream and at least partially condensing the compressed top stream to form a liquid stream,
  decompressing at least a portion of the liquid stream to form a cooled liquid stream and a cooled gas stream; and
  recycling the cooled liquid stream to the top of the distillation column as a reflux;
  wherein the stream of absorbing solvent is reduced and finally discontinued as the temperature at the column top decreases.

The process may include recycling also the cooled gas stream to the distillation column at any point of the distillation column. Conveniently however, a two-phase liquid/gaseous stream obtained upon decompression of the liquid stream is introduced to the top of the distillation column.

The phosgene/absorbing solvent stream obtained at the bottom of the column is likewise recirculated to the isocyanate synthesis.

In reverse, the process can also be easily taken out of operation. This means that with decreasing hydrogen chloride production, a stream of the absorbing solvent is started to be introduced into the distillation column.

The distillation column preferably comprises internals, for example structured packings, random packings or trays, such as may be used in distillation columns. However, it is preferable to use one or more packings as internals.

The mixed stream conveyed to the distillation column derives, for example, from isocyanates production from a primary amine and phosgene. This isocyanate production may be carried out either in the gas phase or in the liquid phase. In the case of gas-phase phosgenation, the stream generally comprises hydrogen chloride and phosgene and any solvent used for quenching the gaseous reaction mixture. In the case of liquid-phase phosgenation, the stream may further comprise reaction solvent, e.g. monochlorobenzene. 1,2-dichlorobenzene, 1,3-dichlorobenzene or 1,4-dichlorobenzene. Generally, phosgene and hydrogen chloride make up for at least 70 wt.-% of the mixed stream.

The mixed stream containing hydrogen chloride and phosgene may be conveyed into the distillation column in a gaseous state. However, in order to support the establishment of an appropriate temperature profile in the column, it may be preferred to partially condense the mixed stream and introduce the mixed stream into the column as a two-phase gaseous/liquid stream.

The mixed stream containing hydrogen chloride and phosgene may be conveyed into the distillation column as a side feed or else fed into the bottom of the distillation column. When the mixed stream is fed into the bottom of the distillation column, the distillation column primarily acts as a rectifying section.

In an embodiment, however, the mixed stream is conveyed into the distillation column as a side feed, the distillation column having a rectifying section above the side feed and a stripping section below the side feed.

Use of a distillation column with a rectifying section and a stripping section achieves improved purification of the phosgene obtained at the bottom. In particular, this renders the phosgene obtained at the bottom substantially free of hydrogen chloride. "Substantially free" is to be understood as meaning that the concentration of hydrogen chloride is in the range of from 10 to 1000 ppm. This allows the phosgene to be recycled into the isocyanate production directly and without further work-up while the absence of hydrogen chloride has the effect that commencement of undesired amine hydrochloride by-products formation occurs only after a delay rather than as soon as the amine is mixed with the phosgene which has the further advantage that the amount of amine hydrochloride formed is kept lower than when phosgene still comprising residual hydrogen chloride is added.

The distillation of the mixed stream is preferably carried out at the pressure at which the stream was withdrawn from isocyanate production. Suitable values for this pressure are generally in the range of from 1 to 10 bar (abs), preferably in the range of from 1.2 to 8 bar (abs) and in particular in the range of from 1.5 to 7 bar (abs).

Accordingly, the stream withdrawn at the top of the distillation column is obtained at a pressure essentially equal to the pressure at which the distillation column is operated or, in other words, is not subjected to pressure-relaxation. The stream withdrawn at the top of the distillation column is preferably compressed to a pressure in the range of from 5 to 25 bar, more preferably to a pressure in the range of from 7 to 22 bar and in particular to a pressure in the range of from 10 to 20 bar. Compressing at least a portion of the essentially hydrogen chloride-comprising stream withdrawn at the top of the column allows the condensation to be carried out at relatively high temperatures with an attendant distinct reduction in energy consumption.

Preferably, the pressure drop during decompressing is at least 5 bar.

The choice of the absorbing solvent is dependent on the ability to dissolve phosgene, and the ideal absorbing solvent should have a high solubility for phosgene, a low solubility for hydrogen chloride and a low volatility. Typically, the absorbing solvent is the solvent used for the phosgenation and is inert in the reaction of amine and phosgene. Preferred absorbing solvents are selected from monochlorobenzene and dichlorobenzene. Typically, monochlorobenzene is used.

Introduction of the absorbing solvent into the distillation column encompasses addition of the absorbing solvent directly into the distillation column or introduction of the absorbing solvent into any stream that is directly or indirectly introduced into the distillation column. Introduction of the absorbing solvent can occur at any point in the top of the distillation column or and/or into the reflux liquid.

As soon as enough hydrogen chloride is available at the top of the column to form a liquid stream, it may, however, be beneficial to mix the absorbing solvent with the liquid stream before decompressing, and to recycle the absorbing solvent into the distillation column with the cooled liquid stream. When flashing a liquid stream consisting predominantly of hydrogen chloride to a low pressure, temperatures of −70° C. and less can occur. At such cold spots in the column top, an absorbing solvent such as monochlorobenzene or dichlorobenzene can easily crystallize and cause clogging. By mixing the absorbing solvent with the liquid stream before decompressing, the temperature drop can be controlled and the remaining liquid hydrogen chloride that has not been vaporized during decompression can serve as a diluent for the absorbing solvent and, thus, crystallization of absorbing solvent can be prevented.

In an embodiment, the compressed top stream is directed to a rectifying column and a stream obtained at the bottom of the rectifying column is recycled to the top of the distillation column. In order to improve the purification of the essentially hydrogen chloride-comprising stream withdrawn at the top of the distillation column, it is advantageous when after compression the essentially hydrogen chloride-comprising stream withdrawn at the top is supplied to a rectifying column and the stream obtained at the bottom of the rectifying column is recycled into the top of the distillation column. It is preferable when the stream obtained at the top of the rectifying column is partially condensed in a condenser, the condensed portion is recycled into the rectifying column and the portion comprising uncondensed gaseous purified hydrogen chloride is withdrawn and sent for further use, for example in hydrochloric acid production or chlorine production by oxidation of the hydrogen chloride.

When the rectifying section of the distillation column is sufficiently dimensioned the rectifying column on the high-pressure side of the compressor may be dispensed with. All what is still required then is condensation of the fraction of hydrogen chloride required for the liquid reflux into the distillation column operated at lower pressure.

It is preferable to employ heat integration measures to conserve energy. Particularly the cold, uncondensed gas stream from the top condenser lends itself to heat integration. Said stream may be utilized for pre-cooling other streams. The cold stream obtained at the top of the column is also usable for energy integration measures. It is also conceivable to use intermediate cooling to minimize energy costs. The opportunities for energy integration and hence for minimizing energy consumption are manifold and are known to those skilled in the art.

In one embodiment, the liquid stream is heat-exchanged in a heat exchanger with the top stream before the top stream is compressed. In a heat exchanger the liquid stream, i.e., the condensed hydrogen chloride-comprising stream, gives off heat to the gaseous top stream, i.e., the hydrogen chloride-comprising stream that is to be condensed, before said stream is compressed. After compression, the hydrogen chloride-comprising stream is cooled down and partially condensed and the uncondensed portion is withdrawn via a gas takeoff. The condensed portion is recycled into the heat exchanger as heat-transfer medium for heating the essentially hydrogen chloride-comprising stream withdrawn at the top.

In a further embodiment, an uncondensed portion of the top stream is heat-exchanged in a heat exchanger with the compressed top stream that is to be condensed. in a heat exchanger the uncondensed portion of the essentially hydrogen chloride-comprising stream absorbs heat from the compressed and hydrogen chloride-comprising stream that is to be condensed. The hydrogen chloride-comprising stream to be condensed is thus pre-cooled before said stream is supplied to the condenser.

In a further embodiment, the method comprises withdrawing a gaseous side stream from the distillation column via a side takeoff, at least partially condensing the side stream in a first cooler, recycling a liquid fraction into the distillation column and supplying a gaseous portion to a second cooler, wherein in the second cooler the gaseous portion is heat-exchanged with the top stream. It is preferable when the stream withdrawn at the top is heated up in a heat exchanger before being supplied to the second cooler. Preferably, the top stream, before being fed to the second cooler, is heat-exchanged with the condensed top stream.

Each of the individual heat integration measures described hereinabove may be implemented individually or in any desired combination.

BRIEF DESCRIPTION OF FIGURE

The invention is illustrated by the accompanying drawing and the examples that follow.

FIG. 1 shows an embodiment of the method according to the invention.

According to FIG. 1, a mixed stream containing hydrogen chloride and phosgene is supplied to lower region 3 of distillation column 1 via feed 5. In the distillation column, the mixed stream is separated by distillation into a phosgene-comprising bottoms stream withdrawn via bottom takeoff 7 and an essentially hydrogen chloride-comprising stream withdrawn at top takeoff 9.

The mixed stream containing hydrogen chloride and phosgene preferably derives from isocyanate production. In one embodiment the pressure at which the distillation is performed is equal to the pressure at which the phosgene- and hydrogen chloride-comprising stream was withdrawn from isocyanate production. In an alternative embodiment the distillation is performed at a pressure below the pressure at which the mixed stream containing hydrogen chloride and phosgene was withdrawn from isocyanate production.

To aid distillation, distillation column 1 comprises internals 11, for example a structured packing or a random packing. Distillation column 1 may alternatively be a tray column.

In accordance with the invention the top stream containing hydrogen chloride is withdrawn via top takeoff 9 and is compressed to a higher pressure in compressor 13. The pressure to which the top stream is compressed is preferably in the range of from 5 to 25 bar.

After compression, the compressed top stream is passed into top condenser 15. The compressed top stream is partially condensed in the top condenser to form a liquid stream. Due to the high pressure, this partial condensation does not necessitate cooling to temperatures that would be necessary had the condensation been carried out at the pressure prevailing at the top of the distillation column. The liquid stream is decompressed in decompression means 17, for example a throttle or a valve, to the pressure prevailing at the top of distillation column 1. This stream thus cools down, while undergoing partial evaporation, to its boiling temperature at column pressure and is recycled into the top of distillation column 1 via return 19. The uncondensed portion of the compressed top stream is withdrawn from top condenser 15 via gas takeoff 21.

In accordance with the invention, an absorbing solvent such as monochlorobenzene is introduced into and mixed with the liquid stream before decompressing via line 23 during the starting-up of the process. Addition of the absorbing solvent prevents phosgene from ascending into the column top as long as there is no or insufficient hydrogen chloride in the system to provide decompression cooling and sufficient reflux of liquefied hydrogen chloride. The stream of absorbing solvent is reduced and finally discontinued as hydrogen chloride is gradually produced and the system can be filled so that the temperature at the column top decreases.

high. Also, in case of leakage there is a considerable risk of releasing a large amount of toxic liquid hydrogen into environment.

EXAMPLE ACCORDING TO THE INVENTION

The comparative example described above is repeated. However no liquid hydrogen chloride from the storage container is supplied. A stream of chlorobenzene of 11640 kg/h at −25° C. is supplied via line 23 and valve 17 to the top of column 1 to obtain a predetermined maximum concentration of 0.1 wt % phosgene in stream 21 (see step 1 in table below).

After a while, enough hydrogen chloride is available and about 500 kg/h of condensate is taken from condenser 15 and fed back together with chlorobenzene via valve 17 to the column in step 2. The feed of chlorobenzene can be reduced to 9684 kg/h to keep the phosgene concentration in stream 21 at 0.1 wt %. After several steps of increasing condensate flow and decreasing chlorobenzene flow, steady-state distillation is reached at step 6.

| | MCB stream | Liquid from | Gas stream 9 | | Bottoms stream 7 | | | | |
|---|---|---|---|---|---|---|---|---|---|
| Stage | 23 kg /h | (15) kg/h | ° C. | wt % Phosgene | Kg/h | ° C. | Wt % HCl | Wt % Phosgene | Wt % MCB |
| 1 | 11640 | 0 | −5.0 | 0.1 | 38750 | −0.5 | 5.5 | 56.7 | 37.8 |
| 2 | 9684 | 500 | −10.6 | 0.1 | 36780 | −2.8 | 5.7 | 59.7 | 34.6 |
| 3 | 7620 | 1000 | −17.2 | 0.1 | 34680 | −5.3 | 6.0 | 63.3 | 30.7 |
| 4 | 5489 | 1500 | −24.9 | 0.1 | 32510 | −7.9 | 6.3 | 67.6 | 26.1 |
| 5 | 3311 | 2000 | −34.5 | 0.1 | 30280 | −10.6 | 6.6 | 72.6 | 20.8 |
| 6 | 0 | 2624 | −52.5 | 0.1 | 26850 | −13.7 | 7.0 | 81.8 | 11.2 |

(MCB = monochlorobenzene)

COMPARATIVE EXAMPLE

A gaseous stream of 35 t/h containing 28.6 wt % HCl, 62.8 wt % phosgene and 8.6 wt % chlorobenzene is taken from the reaction section of an isocyanate plant and subjected to separation in a plant according to FIG. 1.

The gaseous stream emerges from the isocyanate plant at a temperature of 90° C. and a pressure of 2.4 barg. The stream is partially condensed in several steps to obtain a liquid/gas mixed stream at −13.5° C. and 2.3 barg. This stream (5) is fed to the sump of a distillation column (1) operated at a top pressure of 2.2 barg. The packing (11) realizes 20 theoretical stages.

During startup, liquid hydrogen chloride from a storage container (not shown in FIG. 1) is supplied via line 23 and valve 17. The gaseous product at the top (9) mainly consisting of hydrogen chloride is compressed to a pressure of 12.2 barg (13) and partially condensed in condenser (15) at about −23° C. to obtain a liquid stream of 2624 kg/h. The liquid stream is flashed via valve 17 to the top of the distillation column to realize a low-temperature reflux.

The non-condensed gas flow 21 (about 8150 kg/h) from condenser mainly contains HCl with 0.1 wt % phosgene. At the bottom of the distillation column 1, a stream 7 of 26850 kg/h is withdrawn, containing about 7 wt % hydrogen chloride, 81.8 wt % phosgene and 11.2 wt % chlorobenzene.

The storage container holding liquid hydrogen chloride required for startup holds a volume of 5 m³ and is normally filled with liquid HCl at 12.2 barg and kept at temperature below −23° C. The investment for equipment including a pressure-resistant vessel and heat-insulating layers is very This procedure dispenses with the necessity of storing toxic hydrogen chloride and avoids the related investment.

The invention claimed is:

1. A process of separating phosgene and hydrogen chloride, comprising:
conveying a mixed stream containing hydrogen chloride and phosgene into a distillation column;
withdrawing from the distillation column a bottom stream containing phosgene;
withdrawing a top stream containing hydrogen chloride;
compressing at least a portion of the top stream and at least partially condensing the compressed top stream to form a liquid stream, decompressing at least a portion of the liquid stream to form a cooled liquid stream and a cooled gas stream; and
recycling the cooled liquid stream to the top of the distillation column as a reflux;
the process additionally comprising temporarily introducing an absorbing solvent into the distillation column, wherein the absorbing solvent is introduced at the top of the distillation column and/or into the reflux liquid.

2. The process according to claim 1, wherein the absorbing solvent is introduced during starting-up and/or shutting-down of the process.

3. The process according to claim 1, wherein the absorbing solvent is selected from monochlorobenzene and dichlorobenzene.

4. The process according to claim 1, wherein the absorbing solvent is mixed with the liquid stream before decompressing and is introduced into the distillation column with the recycled cooled liquid stream.

5. The process according to claim 1, wherein the pressure drop during decompressing is at least 5 bar.

6. The process according to claim 1, wherein the mixed stream is conveyed into the distillation column as a side feed, the distillation column having a rectifying section above the side feed and a stripping section below the side feed.

7. The process according to claim 1, wherein the compressed top stream is directed to a rectifying column and a stream obtained at the bottom of the rectifying column is recycled to the top of the distillation column.

8. The process according to claim 1, wherein the liquid stream is heat-exchanged in a heat exchanger with the top stream before the top stream is compressed.

9. The process according to claim 1, wherein an uncondensed portion of the top stream is heat-exchanged in a heat exchanger with the compressed top stream that is to be condensed.

10. The process according to claim 1, comprising withdrawing a gaseous side stream from the distillation column via a side takeoff, at least partially condensing the side stream in a first cooler, recycling a liquid fraction into the distillation column and supplying a gaseous portion to a second cooler, wherein in the second cooler the gaseous portion is heat-exchanged with the top stream.

11. The process according to claim 10, wherein the top stream, before being fed to the second cooler, is heat-exchanged with the condensed top stream.

\* \* \* \* \*